United States Patent [19]

Waier et al.

[11] Patent Number: 5,312,937

[45] Date of Patent: May 17, 1994

[54] METHOD FOR THE PREPARATION OF PLATINUM COMPLEXES

[75] Inventors: Steven H. Waier; ChiTang Li, both of Midland; Donna Gyles-Mayon, Saginaw, all of Mich.

[73] Assignee: Dow Corning Corporation, Midland, Mich.

[21] Appl. No.: 133,491

[22] Filed: Oct. 7, 1993

[51] Int. Cl.⁵ .................. C07F 19/00; C07F 15/00; C07F 7/18
[52] U.S. Cl. .................... 556/9; 556/136; 556/431; 556/443; 556/465; 528/15
[58] Field of Search .................... 556/9, 136, 431, 443, 556/465

[56] References Cited

U.S. PATENT DOCUMENTS

| | | | |
|---|---|---|---|
| 2,823,218 | 2/1958 | Speier | 260/448.2 |
| 3,419,593 | 12/1968 | Willing | 260/448.2 |
| 3,474,123 | 10/1969 | Kelly et al. | 260/448.2 |
| 3,775,452 | 11/1973 | Karstedt | 260/429 |
| 4,647,679 | 3/1987 | Panster et al. | 556/9 |
| 5,087,712 | 2/1992 | Volchenskova et al. | 556/137 |
| 5,175,325 | 12/1992 | Brown et al. | 556/9 |
| 5,185,458 | 2/1993 | Huggins | 556/9 |

*Primary Examiner*—José G. Dees
*Assistant Examiner*—Porfirio Nazario-Gonzalez
*Attorney, Agent, or Firm*—Timothy J. Troy

[57] ABSTRACT

The present invention relates to a method for preparing a platinum-organosiloxane complex which comprises (I) reacting (a) a platinous halide having an average crystal size of less than 2500 Angstroms and (b) an organosiloxane having from 2 to 4 silicon-bonded organic groups having from 2 to 6 carbon atoms and having terminal olefinic unsaturation, the remaining silicon-bonded organic substituents being selected from alkyl groups having from 1 to 6 carbon atoms and phenyl groups, wherein said reaction is carried out in the presence of a polar organic liquid which is at least a partial solvent for platinous halide, and (II) neutralizing the reaction mixture of (I). The complexes of the instant invention are useful as catalysts for hydrosilylation reactions.

16 Claims, No Drawings

1

METHOD FOR THE PREPARATION OF PLATINUM COMPLEXES

BACKGROUND OF THE INVENTION

This invention relates to a novel process for the production of complexes of platinum and organosiloxanes and to the use of said complexes.

It is well known in the art of organosilicon chemistry that organosilicon compounds having silicon-bonded hydrogen atoms can be reacted with organic or organosilicon compounds having ethylenic unsaturation in the presence of a platinum compound as catalyst. The use of chloroplatinic acid as such a catalyst has been disclosed by Hook et al. in U.S. Pat. No. 2,823,218.

Willing, in U.S. Pat. No. 3,419,593 disclosed that the compatibility of chloroplatinic acid in organosilicon reaction mixtures can be improved by reacting chloroplatinic acid with an organosilicon compound, preferably an organosiloxane, having silicon-bonded unsaturated groups. A method for preparing platinum complexes of unsaturated siloxanes which are useful as hydrosilylation catalysts was disclosed by Karstedt in U.S. Pat. No. 3,775,452. According to this method an unsaturated organosilicon material is mixed with a platinum halide, typically chloro-platinic acid or sodium or potassium chloroplatinate, and the resulting mixture is then treated with a base to effect the removal of inorganic halogen. Such prior art methods, however, require the presence of water, a very large excess of the vinylsiloxane or long reaction times. The use of a large excess of the vinylsiloxane represents a significant drawback to these type of methods inasmuch as some loss of this relatively expensive reactant occurs as a result of cleavage of the vinyl groups and any remaining excess has to be recovered from the reaction mixture.

Further, it has been discovered that the presence of water contributes to the loss of vinyl groups from the siloxane reactant and increases the need for an excess of the vinylsiloxane. It was suggested by Karstedt in U.S. Pat. No. 3,775,452 (Col. 7, line 40) that the complex can be recovered in admixture with the excess vinylsiloxane and employed as such. However, the presence of the vinylsiloxane can reduce the activity of the platinum as a catalyst. Also, such an impure form of the complex may not be satisfactory for certain applications.

It has been discovered by the present inventors that by employing specific platinum compounds, namely platinous halides, complexes of platinum and organosiloxanes can be obtained by a method which does not require the presence of large excesses of the organosiloxane or of water.

It was suggested by Kelly et al. in U.S. Pat. No. 3,474,123 that complexes of platinous chloride and unsaturated organosiloxanes can be prepared by direct reaction, as in the case of organic complexes of platinum. However, the yields obtained by such a direct reaction are very low and it should be noted that all of the Examples in the '123 patent illustrate the alternative method described therein which involves the additional step of first forming the organic complex.

Brown et al. in U.S. Patent No. 5,175,325 discloses a method for preparing a platinum-organosiloxane complex which comprises reacting a platinous halide with an organosiloxane in which there are present from 2 to 4 silicon-bonded organic groups having from 2 to 6 carbon atoms and terminal olefinic unsaturation, the remaining silicon— bonded organic substituents being selected from alkyl groups having from 1 to 6 carbon atoms and phenyl groups, said reaction being carried out in the presence of a polar organic liquid which is at least a partial solvent for the platinous halide. However, nowhere in Brown et al. is it disclosed that the crystal size of the platinous halide has any effect on the reaction rate of the method of their invention.

SUMMARY OF THE INVENTION

The present invention relates to a method for preparing a platinum-organosiloxane complex which comprises (I) reacting (a) a platinous halide having an average crystal size of less than 2500 Angstroms and (b) an organosiloxane having from 2 to 4 silicon-bonded organic groups having from 2 to 6 carbon atoms and having terminal olefinic unsaturation, the remaining silicon-bonded organic substituents being selected from alkyl groups having from 1 to 6 carbon atoms and phenyl groups, wherein said reaction is carried out in the presence of a polar organic liquid which is at least a partial solvent for platinous halide, and (II) neutralizing the reaction mixture of (I).

It is an object of the present invention to produce complexes which are useful as catalysts for hydrosilylation reactions.

It is also an object of the present invention to provide a method of preparing platinum-organosiloxane complexes without the need to use large excesses of unsaturated organosiloxane reactants.

It is a further object of the present invention to provide a method of preparing platinum-organosiloxane complexes which can be carried out in the absence of water and thereby reduce the formation of by-products in the complexes.

These and other features, objects and advantages of the present invention will be apparent upon consideration of the following detailed description of the invention.

DETAILED DESCRIPTION OF THE INVENTION

The present invention relates to a method for preparing a platinum-organosiloxane complex which comprises (I) reacting (a) a platinous halide having an average crystal size of less than 2500 Angstroms and (b) an organosiloxane having from 2 to 4 silicon-bonded organic groups having from 2 to 6 carbon atoms and having terminal olefinic unsaturation, the remaining silicon-bonded organic substituents being selected from alkyl groups having from 1 to 6 carbon atoms and phenyl groups, wherein said reaction is carried out in the presence of a polar organic liquid which is at least a partial solvent for platinous halide, and (II) neutralizing the reaction mixture of (I).

The platinous halide employed in the method of this invention can be selected from the group consisting of platinum dichloride, platinum dibromide, platinum diiodide, platinum tetrachloride, platinum tetrabromide, platinum tetraiodide, and mixtures thereof, but is preferably the more readily available platinum dichloride. It is critical to the method of the instant invention that the platinous halide have an average crystal size of less than 2500 Angstroms. The crystal size of the platinous halide is measured by X-ray Diffraction (XRD). The XRD technique is well known to those skilled in the art. It is preferred for the method of this invention that the crystal size of the platinous halide is from 500 to 1500 Angstroms.

As the organosiloxane reactant in forming the platinum-organosiloxane complexes there can be employed any cyclic or substantially linear organosiloxanes in which there are from 2 to 4 silicon-bonded organic groups having from 2 to 6 carbon atoms and containing terminal olefinic unsaturation. Such unsaturated groups include hydrocarbon groups for example vinyl, allyl, butenyl and hexenyl but are preferably vinyl. The remaining silicon-bonded organic groups in the organosiloxane reactant are preferably methyl but up to 50% of said remaining groups may be selected from alkyl groups having from 2 to 6 carbon atoms and phenyl groups. Some chain branching may be present in the organo siloxane reactant. Thus it will have in the molecule from about 1.9 to 3.0 total organic groups per silicon atom.

Examples of the operative organosiloxanes are methyl-vinyl- cyclotetrasiloxane, copolymers of dimethylsiloxane and methylvinylsiloxane and copolymers of dimethylsiloxane and phenylmethylvinylsiloxane. The preferred organosiloxanes are those in which at least two of the vinyl groups are present on adjacent silicon atoms. Most preferred is 1,3-divinyltetramethyldisiloxane.

The polar organic liquid which must be present in the reaction mixture of the method of this invention should be at least a partial solvent for the platinous halide, that is, it should be capable of solubilizing at least some of the platinous halide present in the reaction mixture. It is believed that the reaction proceeds by way of the formation of a weak complex between the polar liquid and the platinous halide. This complex then breaks down and reacts with the organosiloxane via the ligands and olefinic groups to form the desired platinum-organosiloxane complex. Suitable polar organic liquids are therefore those which react with the platinous halide to provide a first complex which is soluble in the polar organic liquid and in which the ligands are displaceable by the olefinic e.g. vinyl groups in the organosiloxane to yield the desired platinum organosiloxane complex. Such polar liquids include amides, for example dimethylformamide, ketones, for example butanone, and acetone and crown ethers, the preferred polar liquids being the amides and ketones. The proportion of polar liquid present is not narrowly critical but preferably falls within the range from 1 to 20 moles of polar liquid per mole of platinous halide.

The organosiloxane is preferably employed in a proportion of at least 3.5 moles per mole of the platinous halide. In order to achieve minimum reaction times the organosiloxane should be present in stoichiometric excess, that is more than 8 vinyl groups per platinum atom. Very large excesses of the organosiloxane are, however, best avoided. We have found that such large excesses can lead to the presence of undesirable amounts of by-product oligomers.

In carrying out the method of this invention the reactants are mixed and reacted at elevated temperatures. Some reaction may occur at temperatures as low as 40° C but it is preferred to employ temperatures in the range from about 50° C. to 120° C.

Step (II) of the method of this invention comprises neutralizing the reaction mixture of (I). Neutralization of the mixture of Step (I) is accomplished by mixing the reaction product of Step (I) with a hydrocarbon solvent such as heptane, toluene or xylene and a basic buffer solution at elevated temperature. It is preferred for the method of the present invention that the neutralization of the reaction product of Step (I) be carried out at a temperature of from 40° to 50° C. The buffer solution is a mixture of deionized water and a salt selected from the group consisting of sodium bicarbonate, calcium carbonate, magnesium oxide, or magnesium carbonate. It is preferred in the method of this invention to employ sodium bicarbonate salt.

In addition, up to 25% by weight of an organosiloxane such as a polydimethylmethylsiloxane, a vinyl terminated polydimethylsiloxane, or a polyorganosiloxane having silicon-bonded olefinically- unsaturated groups such as tetramethyldivinyldisiloxane may be added prior to or after step (II).

It is not necessary to dry the reactants beforehand but in order to avoid the formation of undesired oligomeric species the reaction is best carried out in the absence of added water. On completion of the reaction the non polar solvent, if used, may be removed by distillation, if necessary or desired under reduced pressure. The polar organic liquid may be allowed to remain in the platinum siloxane reaction product but can be removed, if desired, under reduced pressure. Where its boiling point permits, any excess of the organosiloxane reactant may be removed by distillation. However, the platinum-organosiloxane complexes have been found to be unstable during storage in the pure state.

The method of this invention has the advantage of providing pure platinum-organosiloxane complexes without the need to use large excesses of the unsaturated organosiloxane reactant. It can also be carried out in the absence of water, thereby reducing the formation, and presence in the desired product, of oligomeric by-products.

The platinum-organosiloxane complexes prepared by the method of this invention are useful as catalysts. They are particularly useful as catalysts for the well-known hydrosilylation reactions in organosilicon chemistry. In another aspect therefore the invention includes a process comprising reacting (i) a silicon compound having in the molecule at least one silicon-bonded hydrogen atom with (ii) an organic or organosilicon substance containing aliphatic carbon atoms linked by multiple bonds. In such hydrosilylation reactions the organosilicon compounds having $\equiv$SiH groups may be silanes, siloxanes or other silicon containing polymers, for example $HSiCl_3$, $CH_3SiHCl_2$, $HSi(OC_2H_5)_3$, $C_6H_5SiHCl_2$, $C_6H_5SiHCH_3Br$, $(CH_3)_2SiHCl$, $C_2H_5SiH_2Cl$, $CH_3SiH(OCH_3)_2$, methylhydrogen polysiloxanes and copolymers of methylhydrogensiloxane units and, for example, dimethylsiloxane units, trimethylsiloxane units and phenylethylsiloxane units. The nature of the silicon-bonded substituents present in addition to the hydrogen atoms is not critical but normally such substituents will comprise halogen atoms, alkoxy radicals, preferably having less than 6 carbon atoms and monovalent hydrocarbon or halogenated hydrocarbon radicals having from 1 to 18 inclusive carbon atoms.

The compounds containing carbon atoms linked by multiple bonds may be organic, for example pentene-1, hexene-1, heptene-1, acetylene, butadiene, vinylacetylene, cyclohexene, styrene, allyl bromide, vinyl acetate, allyl alcohol or an allyl ether of a poly(alkylene oxide); or they may be organosilicon, for example $(CH_3)_2(CH_2=CH)SiCl$, $(CH_2=CHCH_2)(CH_3)SiBr_2$, $(CH_2=CH)Si(C_2H_5)_2Cl$, $(CH_2=CH)Si(OCH_3)_3$ and organosiloxanes and polysiloxanes containing silicon-bonded vinyl, allyl or hexenyl radicals. Any remaining silicon-bonded substituents in the unsaturated organosilanes and organosiloxanes may be, for example, halogen atoms, alkoxy radicals having less than 6 carbon atoms and monovalent hydrocarbon or halogenated hydrocarbon radicals having from 1 to 18 inclusive carbon atoms.

The reaction of silicon-bonded hydrogen atoms with unsaturated radicals is well-known and may be employed for the preparation of organofunctional and other organosilicon compounds and in the preparation of elastomeric or resinous organosilicon products for coating, encapsulating and other applications. The hydrosilylation reaction may be performed at atmospheric, sub-atmospheric or super-atmospheric pressures, in the presence or absence of solvents, and at temperatures ranging from below 20° C. up to and in excess of 150° C.

For certain applications it is desirable to include in compositions comprising (i), (ii) and the platinum catalyst a substance which inhibits and delays the reaction between (i) and (ii). Among known inhibiting substances are the alkyl, alkoxyalkyl and allyl esters of maleic and fumaric acids. According to a further aspect of the invention we have found that, if desired, the platinum-organosiloxane complexes of this invention may be prereacted with such known inhibitor substances to provide a preformed inhibited hydrosilylation catalyst.

Particle size data was generated for three samples of $PtCl_2$ on a Malvern Particle Size Analyzer. The data is reported as a diameter at which a given percentage of the particles are said to be equal or smaller than the reported value.

The crystal size of $PtCl_2$ was measured by X-ray Diffraction (XRD). The XRD procedure for measuring the crystallite size of the platinous halide was as follows: the platinous halide was placed in a x-ray powder diffractometer (such as a Siemen's D-5000 Theta-Theta type device) equipped with a graphite monochromator, a scintilation counter, a personal computer, an MPA board, printers, and a Cu tube operated at 40 kV and 30 mA. The platinous halide material is normally run from 10 to 66 degree 2 Theta at 1 degree per minute. A peak at 22 degree 2-Theta is often chosen to measure the line broadening and later the crystallite size. The crystallite size is determined from the Scherrer equation $S=W/PcosT$ where S is size (A (Angstroms), W is the wavelength (Angstroms), P is the net line breadth due to size factor, and T is 2-Theta/2. A standard material such as a single crystal of silicon is needed to accurately define the line broadening due to the instrumental factor.

The following Examples in which the parts are expressed by weight in grams (g), crystal size is expressed in Angstroms (A), and particle size is expressed in microns (um) illustrate the invention.

EXAMPLES 1–5

The crystal size of 5 Samples of $PtCl_2$ was measured by X-ray Diffraction (XRD) as described hereinabove. The crystal sizes of the samples ranged as follows: 3073 A(Angstroms), 1850 A, 1665 A, 1049 A, and 915 A, respectively. Two grams of each sample was then tested in the following reaction.

A mixture of 2g (grams) of a sample of platinum (II) dichloride ($PtCl_2$) having a crystal size of 3073 A, 10g of methylethylketone, and 20g of tetramethyldivinyldisiloxane was heated to 85° C. with stirring for 5–10 hours. The reaction mixture was then cooled to ambient temperature and filtered through a glass microfilter. The filter was then dried in an oven at 70° C. and weighed to determine the net amount of precipitate that was filtered. The same reaction procedure was followed for testing the PtCl, samples having a crystal size of 1850 A, 1665 A, 1049 A, and 915 A, respectively.

The reaction rates for the various crystal sizes of $PtCl_2$ were measured as follows: The net precipitate at the end of the reaction was dried, weighed and recorded. This number was divided by the starting weight of $PtCl_2$ (i.e. approximately 2g) and the resulting value was designated as "% Unreacted Material". The higher that percentage, the more $PtCl_2$ that was left unreacted and therefore had a slower reaction rate. The reactions were carried out under standardized conditions (same equipment, mix rates, stoichiometric amounts of material, etc.). The reaction rates for Examples 1–5 are reported in Table I below. Example 2 was analyzed and it was discovered that the $PtCl_2$ contained Pt(0) metal which appeared as unreacted in the final precipitate thus the percentage of unreacted material in Example 2 is artificially high. It is clear from the data in Table I that the lower the crystal size of the $PtCl_2$ the more dramatically the reaction rate increased. Thus there is a clear correlation between the crystal size of the platinous halide and rate at which the reaction runs to completion.

TABLE I

| Example | Crystal Size (A) | Reaction Time (hrs) % Unreacted Material | | | | |
|---------|------------------|------|------|------|------|------|
|         |                  | 5.0  | 6.0  | 7.0  | 7.5  | 8.0  |
| 1 | 3073 | 20.9 | 11.8 | —   | —    | 5.4  |
| 2 | 1850 | 31.2 | 23.7 | —   | 15.4 | 12.4 |
| 3 | 1665 | —    | 8.8  | —   | —    | —    |
| 4 | 1049 | 2.8  | —    | 2.2 | —    | —    |
| 5 | 915  | 1.2  | —    | —   | —    | —    |

COMPARATIVE EXAMPLES 6–8

Particle size data was generated for three samples of $PtCl_2$ on a Malvern Particle Size Analyzer. The data is reported as a diameter at which a given percentage of the particles are said to be equal or smaller than the reported value. The data is reported in Table II below (um = microns).

TABLE II

| Comparative Example | Particle Size Distribution | | |
|---------------------|--------|---------|----------|
|                     | 10%    | 50%     | 90%      |
| 6 | 5.6 um | 25.1 um | 103.0 um |
| 7 | 4.9 um | 18.7 um | 91.0 um  |
| 8 | 1.6 um | 8.3 um  | 61.7 um  |

A mixture of 2g (grams) of each sample of platinum (II) dichloride ($PtCl_2$) in Table II hereinabove, 10g of methylethylketone, and 20g of tetramethyldivinyldisiloxane was heated to 85° C. with stirring for 5–10 hours. The reaction mixture was then cooled to ambient temperature and filtered through a glass microfilter. The filter was then dried in an oven at 70° C. and weighed to determine the net amount of precipitate that was filtered.

The reaction rates for the various particle sizes of $PtCl_2$ were measured as follows: The net precipitate at the end of the reaction was dried, weighed and recorded. This number was divided by the starting weight of PtCl$_2$ (i.e. approximately 2g) and the resulting value was designated as "% Unreacted Material". The higher that percentage, the more PtCl$_2$ that was left unreacted and therefore had a slower reaction rate. The reactions were carried out under standardized conditions (same equipment, mix rates, stoichiometric amounts of material, etc.). The reaction rates for Comparative Examples 6–8 are reported in Table III below. It is clear from the data in Table III that no correlation exists between exists between particle size and reaction rate.

TABLE III

| Comparative Example | Reaction Time (hrs) | | | | |
|---|---|---|---|---|---|
| | 5.0 | 6.0 | 7.0 | 7.5 | 8.0 |
| | % Unreacted Material | | | | |
| 6 | 1.2% | — | — | — | — |
| 7 | — | 8.8% | — | — | — |
| 8 | 31.2% | 23.7% | — | 15.4% | 12.4% |

EXAMPLES 9–14

A catalyst was then prepared by stripping the reaction mixture of each of Examples 1–5, and then adding to each a mixture of 0.35 g of tetramethyldivinyldisiloxane, 15 g of toluene, 1.2 g of sodium bicarbonate, and 15 g of water. This mixture was then stirred. The resulting aqueous layer was then phase separated and an equivalent amount of water was then added to the remaining particulate phase. This mixture was then stirred for one hour and was again subjected to the phase separation procedure. The remaining platinumtoluene layer was then stripped. Next the final net weight amount of catalyst was then subsequently diluted with tetramethyldivinyldisiloxane (2X the amount of catalyst and a vinyl endblocked polydimethylsiloxane (27X the amount of catalyst). Each of the products of Examples 9–14 was a pale yellow oil.

It should be apparent from the foregoing that many other variations and modifications may be made in the compounds, compositions and methods described herein without departing substantially from the essential features and concepts of the present invention. Accordingly it should be clearly understood that the forms of the invention described herein are exemplary only and are not intended as limitations on the scope of the present invention as defined in the appended claims.

That which is claimed is:

1. A method for preparing a platinum-organosiloxane complex which comprises:
   (I) reacting
      (a) a platinous halide having an average crystal size of less than 2500 Angstroms; and
      (b) an organosiloxane having from 2 to 4 silicon bonded organic groups having from 2 to 6 carbon atoms and having terminal olefinic unsaturation, the remaining silicon- bonded organic substituents being selected from alkyl groups having from 1 to 6 carbon atoms and phenyl groups; wherein said reaction is carried out in the presence of a polar organic liquid which is at least a partial solvent for platinous halide; and
   (II) neutralizing the reaction mixture of (I).

2. A method according to claim 1, wherein the platinous halide is selected from the group consisting of platinum dichloride, platinum dibromide, platinum diiodide, platinum tetrachloride, platinum tetrabromide, platinum tetraiodide, and mixtures thereof.

3. A method according to claim 2, wherein the platinous halide is selected from the group consisting of platinum dichloride, platinum tetrachloride, and mixtures thereof.

4. A method according to claim 1, wherein the crystal size of the platinous halide is from 500 to 1500 Angstroms.

5. A method according to claim 1, wherein the organosiloxane is selected from the group consisting of methylvinylcyclotetrasiloxane, copolymers of dimethylsiloxane and methylvinylsiloxane, and copolymers of dimethylsiloxane and phenylmethylvinylsiloxane.

6. A method according to claim 1, wherein the organosiloxane is 1,3-divinyltetramethyldisiloxane.

7. A method according to claim 1, wherein the polar organic liquid is selected from the group consisting of amides, ketones, and crown ethers.

8. A method according to claim 7, wherein the ketones are selected from the group consisting of butanone and acetone.

9. A method according to claim 1, wherein (II) is carried out by:
   (i) admixing a basic buffer solution and a hydrocarbon solvent with the mixture of (I) at elevated temperatures;
   (ii) removing salts and volatile organic solvents from the admixture of (i).

10. A method according to claim 9, wherein the buffer solution is a mixture of deionized water and a salt selected from the group consisting of sodium bicarbonate, calcium carbonate, magnesium oxide, and magnesium carbonate.

11. A method according to claim 10, wherein the salt is sodium bicarbonate.

12. A method according to claim 9, wherein the hydrocarbon solvent is selected from the group consisting of heptane, toluene, and xylene.

13. A method according to claim 1, wherein the method further comprises the step of mixing the platinum-organosiloxane complex with a polyorganosiloxane.

14. A method according to claim 13, wherein the polyorganosiloxane is selected from the group consisting of polydiorganosiloxanes and polyorganosiloxanes having silicon-bonded olefinically unsaturated groups.

15. A method according to claim 14, wherein the polyorganosiloxane having silicon-bonded olefinically unsaturated groups is selected from the group consisting of tetramethyldivinyldisiloxane and vinyl terminated polydiorganosiloxanes.

16. A method according to claim 15, wherein the vinyl terminated polydiorganosiloxane is a vinyl terminated polydimethylsiloxane.

* * * * *